United States Patent [19]
Choi et al.

[11] Patent Number: 5,871,979
[45] Date of Patent: Feb. 16, 1999

[54] **METHOD FOR MASS PRODUCTION OF TAXOL BY SEMI-CONTINUOUS CULTURE WITH *TAXUS CHINENSIS* CELL CULTURE**

[75] Inventors: Hyung-Kyoon Choi, Taejon, Rep. of Korea; Tom Lee Adams, Millbrae; Roy William Stahlhut, Belmont, both of Calif.; Sang-Ic Kim, Seoul, Rep. of Korea; Jeong-Hwan Yun, Taejon, Rep. of Korea; Bong-Kyu Song, Taejon, Rep. of Korea; Jin-Hyun Kim, Taejon, Rep. of Korea; Jun-Seog Song, Taejon, Rep. of Korea; Seung-Suh Hong, Taejon, Rep. of Korea; Hyun-Soo Lee, Seoul, Rep. of Korea

[73] Assignee: Samyang Genex Co., Ltd., Seoul, Rep. of Korea

[21] Appl. No.: 652,492

[22] PCT Filed: Apr. 27, 1996

[86] PCT No.: PCT/KR96/00060

§ 371 Date: May 28, 1996

§ 102(e) Date: May 28, 1996

[87] PCT Pub. No.: WO96/34110

PCT Pub. Date: Oct. 31, 1996

[30] Foreign Application Priority Data

Apr. 27, 1995 [KR] Rep. of Korea ....................... 95-10204

[51] Int. Cl.$^6$ .................................................... C12P 17/02
[52] U.S. Cl. ..................... 435/123; 435/240.4; 435/244; 435/240.46; 435/240.48; 549/510; 549/511
[58] Field of Search ................................ 435/123, 240.4, 435/244, 240.46, 240.48; 549/510, 511

[56] References Cited

U.S. PATENT DOCUMENTS 5,019,504   5/1991   Christen et al. .
5,279,953   1/1994   Stahlhut .
5,344,775   9/1994   Smith .
5,407,816   4/1995   Bringi et al. .
5,637,484   6/1997   Yukimune et al. ..................... 435/123

FOREIGN PATENT DOCUMENTS

WO 92/13961   8/1992   WIPO .
WO 93/10253   5/1993   WIPO .

OTHER PUBLICATIONS

E.R.M. Wickremesinhe and R. N. Arteca, Taxus Cell Suspension Cultures: Optimizing Growth and Production of Taxol, J. Plant Physiol, 144:183–188 (1994).

R.E.B. Ketchum, D.M. Gibson & L. Greenspan Gallo, Media Optimization for Maximum Biomass Production in Cell Cultures of Pacific Yew, Plant Cell, Tissue and Organ Culture, 42:185–193 (1995).

A.G. Fett–Neto et al., Kinetics of Taxol Production, Growth and Nutrient Uptake in Cell Suspensions of *Taxus cuspidata*.

*Primary Examiner*—Irene Marx
*Attorney, Agent, or Firm*—Darby & Darby

[57] ABSTRACT

The present invention relates to a method for mass production of taxol by semi-continuous culture of Taxus genus plant with a high yield. According to the present invention, taxol can be prepared with a high yield, by employing semi-continuous culture of Taxus genus plant cell, which comprises: (i) inoculating Taxus genus plant cell on a medium containing 1 to 10% (w/v) sugar, and incubating it; and, (ii) transferring 1/10 to 1/2 volume of the culture obtained in the step (i) to a fresh medium and repeating the step (i), adding 1 to 10% (w/v) sugar to the remnant culture and incubating to the time of maximum production of taxol.

4 Claims, 4 Drawing Sheets

METHOD FOR MASS PRODUCTION OF TAXOL BY SEMI-CONTINUOUS CULTURE WITH *TAXUS CHINENSIS* CELL CULTURE

BACKGROUND OF THE INVENTION

1. Field of the Invention

The present invention relates to a method for mass production of taxol from Taxus genus plant cell culture, more specifically, to a method for mass production of taxol by semi-continuous culture of Taxus genus plant cell with a high yield.

2. Description of the Prior Art

Taxanes are diterpene compounds containing a taxane skeleton. For example, taxol is famous as the first identified compound with a taxane ring which was isolated from the bark of the pacific yew, *Taxus brevifolia,* which is effective for the treatment of leukemia and cancer. Recently, it has been reported that: taxol is capable of curing approximately 30%, 50% and 20% of ovarian, breast and lung cancer patients, respectively, by inhibiting depolymerization of microtubules (see: E. K. Rowinsky et al., J. Natl. Cancer. Inst., 82:1247–1259 (1990)).

On the other hand, total chemical synthesis, semi-synthesis and extraction methods have been employed to prepare taxol.

The total chemical synthesis method, however, has not been practically applied in the art, since it requires very expensive chemical reagents and the yield is not so high, which can be expected from the complicated chemical structure of taxol.

The semi-synthesis method employing precursors such as 10-deacetylbaccatin III, has revealed some drawbacks since it essentially entails complicated and multiple steps of isolating and purifying the taxol precursors from Taxus genus plant and transforming the precursors to taxol.

In this regard, the extraction method by which taxol can be isolated from Taxus genus plants in a direct manner, has prevailed in the art, since it has the advantage of economy. However, the said method has proven to be less satisfactory in the sense that it essentially requires a large amount of yew trees to purify taxol, which finally gives rise to the serious environmental disruption.

Accordingly, the ability of total chemical synthesis, semi-synthesis and extraction method to supply taxol for world-wide chemotherapeutic use is not assured; and, there are strong reasons for exploring and developing alternative means of taxol production.

As a promising alternative to solve said problems, the cell culture method for taxol production has been proposed in the art.

The cell culture-based process for taxol production, unlike the prior art, has the following advantages as followings: first, taxol can be produced in a steady manner, regardless of fluctuation of supply of yew plants due to the damage by blight and harmful insects, etc.; secondly, cell cultures can be propagated in large bioreactors, from which taxol can be massively produced by manipulating culture conditions; thirdly, cell cultures produce a simpler spectrum of compounds compared to other prior art methods, considerably simplifying separation and purification; fourthly, a cell culture process can adapt quickly to rapid changes in demand better than the other methods; fifthly, a cell culture process can produce taxol as well as taxane precursors such as baccatin that can be converted to taxol.

Methods for producing taxol by utilizing cultured plant cells have been described in the art:

U.S. Pat. No. 5,019,504 discloses a method for producing taxol and its derivative utilizing cultured cells of *Taxus brevifolia*. However, the yield of taxol described therein is 1–3 mg/L, which is insufficient for industrial application. Besides, the production of taxol by the cell culture is unstable and even when a primary cell of high productivity can be obtained by selection, it is difficult to keep its content by subculturing (see: E. R. M. Wickremesine et al., World Congress on Cell and Tissue Culture (1992)).

U.S. Pat. No. 5,015,744 teaches a semi-synthetic method from baccatin III, which is a precursor in biosynthesis of taxol. By the use of the plant tissue culture, a raw material for the semi-synthetic process such as baccatin III can be produced, thus the plant tissue culture can also be utilized for taxol production by the above-mentioned semi-synthetic process.

WO 93/17121 offers a method for taxol production by cell culture of Taxus genus plant while changing composition of medium, growth rate, and production rate, etc. In case of *Taxus chinensis,* 24.1 mg/L of taxol can be obtained in 18 days of culture and the biomass doubles every 2.5 days.

All of these patents describes methods for mass production of taxol by employing batch culture; there is no teaching in said patents on, nor is there anticipated, semi-continuous culture of a taxol-producing cell line.

Under the circumstances, U.S. Pat. No. 5,407,816 describes that *Taxus chinensis* cells are inoculated to a nutrient medium to form a suspension which is, in turn, cultivated to form a suspension culture which is, in turn, subcultured in the other nutrient medium to form a producing culture, and which finally gives taxol and taxanes in a yield of 153 mg/L. The said method has considerably improved the productivity of taxol, however, it has been proven less satisfactory in the sense that it essentially requires so many different nutrient media whose compositions are so complicated, and high productivity can be realized under rather a limited growth condition.

Therefore, there is a continued need to develop a practical and simple method for taxol production, which is able to meet the requirement of high productivity which is a critical factor to determine whether it can be utilized in industrial applications or not.

SUMMARY OF THE INVENTION

In accordance with the present invention, it has been discovered that taxol can be produced with a high degree of efficiency, by the semi-continuous culture of a novel taxol-producing cell line, *Taxus chinensis* SYG-1.

A primary object of the present invention is, therefore, to provide a method for mass production of taxol by semi-continuous culture.

The other object of the invention is to provide a novel taxol-producing cell line isolated from *Taxus chinensis*.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

Figure 1:
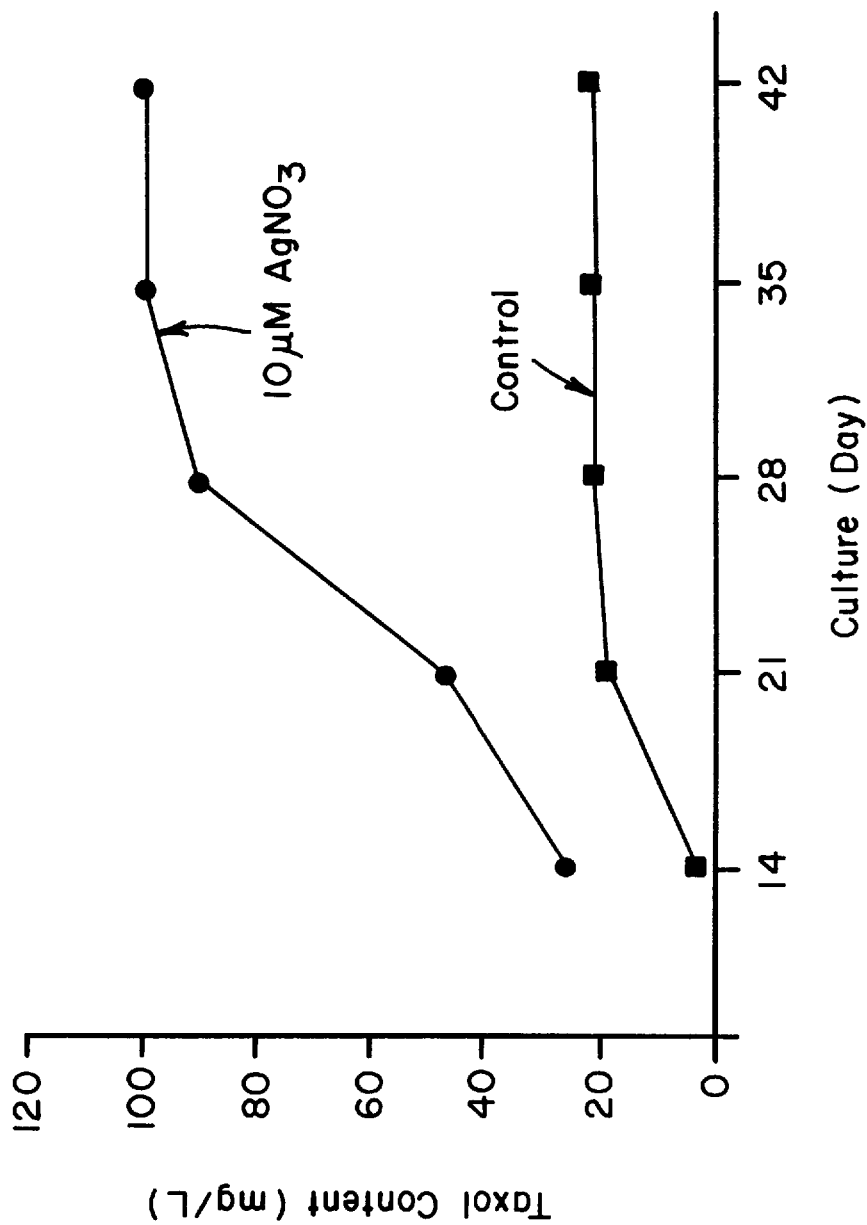
FIG. 1 is a graph showing the effect of $AgNO_3$ on the taxol productivity.

The present inventors first developed a taxol-producing cell line, based on the callus induced from *Taxus chinensis*, and compared the cell line with those known in the art. From the comparative studies on the morphological, physiological and growth condition of the taxol-producing cell lines, it has been determined that the newly developed cell line is a novel one which is somewhat different from those of prior art, in light of taxol productivity, mode of taxol secretion, etc. Accordingly, the cell line was named *Taxus chinensis* SYG-1 (hereinafter, referred to as "SYG-1" for convenience) and it was deposited with an International Depositary Authority (IDA), Taegon 305-600, Republic of Korea, the Korean collection for Type Cultures (KCTC), #52 Oun-dong, Yusong-ku, on Mar. 14, 1996, under an accession number of KCTC 0232BP.

Then, the inventors optimized the growth condition of the cell line of the invention, and determined that: SYG-1 cells grown well on B5 medium, most preferably B5 medium supplemented with 20 $\mu$M NAA (naphthoxyacetic acid), 0.4 $\mu$M BAP (6-benzylaminopurine), 1 g/L casein hydrolysate and 30 g/L sucrose, under a condition of a temperature of 24° C., at an agitation speed of 150 rpm. On the other hand, effects of $AgNO_3$, $NH_4$-citrate and maltose on the productivity of taxol were also examined, and the inventors concluded that their addition considerably improved the productivity of taxol.

According to the present invention, taxol can be prepared with a high yield, by employing semi-continuous culture of SYG-1, which comprises:

(i) inoculating Taxus genus plant cell on a medium containing 1 to 10% (w/v) sugar, and incubating it; and, (ii) transferring 1/10 to 1/2 volume of the culture obtained in the step (i) to a fresh medium and repeating the step (i), adding 1 to 10% (w/v) sugar to the remnant culture and incubating to the time of maximum production of taxol.

At the beginning of culture, $AgNO_3$ may be added to Taxus genus plant cell culture which is incubated for 10 to 20 days, more preferably 10 to 15 days, at a concentration of 1 to 15 $\mu$M, more preferably 5 to 10 $\mu$M. Furthermore, $NH_4$-citrate and maltose may be added to the culture after 5 to 30 days, more preferably 5 to 10 days of incubation, at a concentration of 1 to 15 mM, more preferably 1 to 10 mM and 1 to 10% (w/v), more preferably 1 to 5% (w/v), respectively.

After 5 to 30 days of incubation, 1/10 to 1/2 volume of total culture is transferred to other flask containing fresh medium whose contents are the same as the one employed at the beginning of the culture, and started a cycle of culture. Then, maltose, 1 to 10% (w/v), more preferably 1 to 5% (w/v) was added to the remnant culture equivalent to 9/10 to 1/2 volume of total culture, and incubated for 30 to 60 days in which taxol production is maximized. At this time, incubation was made at 24° C., agitation speed of 150 rpm under a dark condition.

Taxus genus plant employed in the method of the present invention includes *Taxus brevifolia, Taxus canadensis, Taxus cuspidata, Taxus baccata, Taxus globosa, Taxus floridana, Taxus wallichiana, Taxus media* and *Taxus chinensis*, however, *Taxus chinensis* SYG-1 which is newly developed by the inventors, is most preferably employed therein.

According to the method of present invention, the productivity of taxol to the level of 300 mg/L, after 42 to 49 days incubation, is observed, when *Taxus chinensis* SYG-1 is employed in the semi-continuous culture with the addition of $AgNO_3$, $NH_4$-citrate and maltose to improve the productivity of taxol.

Quantitative Analysis of Taxol

Taxol which is produced from the culture of *Taxus chinensis* SYG-1 according to the method of the present invention, is quantitatively assayed by employing high performance liquid chromatography under a specific condition described in Table 1 below.

TABLE 1

| Condition for quantitative assay of taxol | |
|---|---|
| Instrument | HPLC (Waters, U.S.A.) |
| Column | Capcell Pack $C_{18}$ UG 120 (length: 250 mm, inner diameter: 4.6 mm) |
| Column temp. | 40° C. |
| Mobile phase | $CH_3CN$: water (20~100% gradient) |
| Fluid speed | 1.0 ml/min |
| Injection volume | 10 $\mu$l |
| Detector | UV (227 nm), ATTE = 3 |

The present invention is further illustrated in the following examples, which should not be taken to limit the scope of the invention.

EXAMPLE 1

Induction and Characterization of Callus From *Taxus chinensis*

The cell line of the present invention was isolated from *Taxus chinensis* by way of callus induction. When plant tissue was incubated on a proper medium containing a hormone, undifferentiated cell of callus was induced: Tissues from bark, needles, stems and roots of *Taxus chinensis* were washed with tap water and sterilized with Ca-hypochloride solution for 20 to 30 min. Then, the sterilized tissue was washed with distilled water 2 to 3 times, chopped to have a length of 1 cm, and transferred to B5 medium (see: Gamborg et al., Can. J. Biochem., 46:417–421 (1968)) supplemented with 20 $\mu$M NAA (naphthoxyacetic acid), 0.4 $\mu$M BAP (6-benzylaminopurine), 1 g/L casein hydrolysate and 30 g/L sucrose after solidifying with 0.2% (w/w) gelite, and incubated at a temperature of 24° to 26° C. for 2 to 6 weeks under a dark condition to induce the callus of interest.

The growth medium for callus was selected by transferring the callus to several media well known in the art, e.g., MS (see: Murashige, T. and F. Skoog, F., Physiol. Plant, 5:473 (1962)), SH (see: Schenk and Hilderbrandt, Can. J. Bot., 50:199–204 (1972)), WPM (see: Lloyd and Mccown, Int. Plant Prop. Soc. Proc., 30:421–427 (1981)) and B5 media (see: supra), respectively, and observing the growth pattern of the callus by naked eye. From the results above, it was determined that the callus showed good growth on B5 medium containing 20 $\mu$M NAA, 0.4 $\mu$M BAP and 2 g/L casein hydrolysate.

Then, studies on the morphology, physiology and growth condition were made for the cell line thus induced, and compared with those of known in the art; and, the results were summarized in Tables 2 and 3 below. As can be seen in Tables 2 and 3, it was determined that the cell line which has been developed in the invention has a distinction over those of prior art, in light of taxol productivity and mode of taxol secretion, etc. Accordingly, the cell line was named *Taxus chinensis* SYG-1 and was deposited with an International Depositary Authority (IDA), the Korean Collection for Type Cultures (KCTC) on Mar. 14, 1996, under an accession number of KCTC 0232BP.

TABLE 2

Morphology and growth condition of *Taxus chinensis* SYG-1

| *Taxus chinensis* SYG-1 | Characteristics |
| --- | --- |
| Size | 50–150 $\mu$m |
| Mobility | (−) |
| Agglutination | Weak |
| Aggregation | (+) |
| Adaptation to shear stress | Strong |
| Color of culture | Weak brown |
| Culture temperature | 24° C. |

TABLE 3

Comparison of characteristics of cell lines of the invention and prior art

| Characteristics | SYG-1 | USP 5407816 | USP 5019504 | WO 92/13961 |
| --- | --- | --- | --- | --- |
| Secretion mode of taxol | intra-cellular | extra-celluar | not clear | not clear |
| Light-requirement | dark | light | dark | dark |
| Taxol productivity | ~300 mg/L | 153 mg/L | 1–3 mg/L | 0.04% DCW |

EXAMPLE 2

Suspension Culture of SYG-1

To select the most preferred medium for the suspension culture of SYG-1, the cell line was transferred to MS, SH, WPM and B5 media, respectively, and the growth pattern was observed analogously in Example 1, which resulted that SYG-1 cell was well grown on B5 medium containing 20 $\mu$M NAA, 0.4 $\mu$M BAP and 2 g/L casein hydrolysate, like the callus. In addition, it was also determined that SYG-1 cell was well grown at a temperature of 24° C., at an agitation speed of 150 rpm.

A serial cultivation of the callus was made every 4 weeks in a case of solidified medium, while transferring a part of tissue by the aid of forceps: A piece of the callus was maintained on the plate of solid medium. Then, the callus maintained on the solid medium was inoculated into a small volume of B5 medium, and small amounts of medium were supplemented to the culture, as the cells grew to increase total volume of culture. Then, well grown cell lines were diluted in the modified B5 medium contained in 500 ml Erlenmeyer flask at a ratio of 1/5 (v/v), and inoculated into suspension culture medium every two weeks.

EXAMPLE 3

Effect of AgNO$_3$ on the Taxol Productivity

It has been well known that AgNO$_3$ is an antagonist of the plant hormone, ethylene, which effects on the plant cell growth and secondary metabolite production. Accordingly, the present inventors tested the effect of AgNO$_3$ on the taxol production in a suspension culture of SYG-1.

To a 250 ml of Erlenmeyer flask, was poured 75 ml of B5 medium containing 10 $\mu$M AgNO$_3$ and 25 ml of 14 day old cell culture was inoculated into this medium, and incubated in an analogous manner described in Example 2. Then, the productivity of taxol was compared with a control which does not contain AgNO$_3$ (see: FIG. 1). As can be seen in FIG. 1, it was clearly determined that the amount of taxol produced, 98.95 mg/L when AgNO$_3$ was added to a medium (-●-), was 4.7 times the control (-O-).

EXAMPLE 4

Effect of NH$_4$-citrate on the Taxol Productivity

Figure 2:
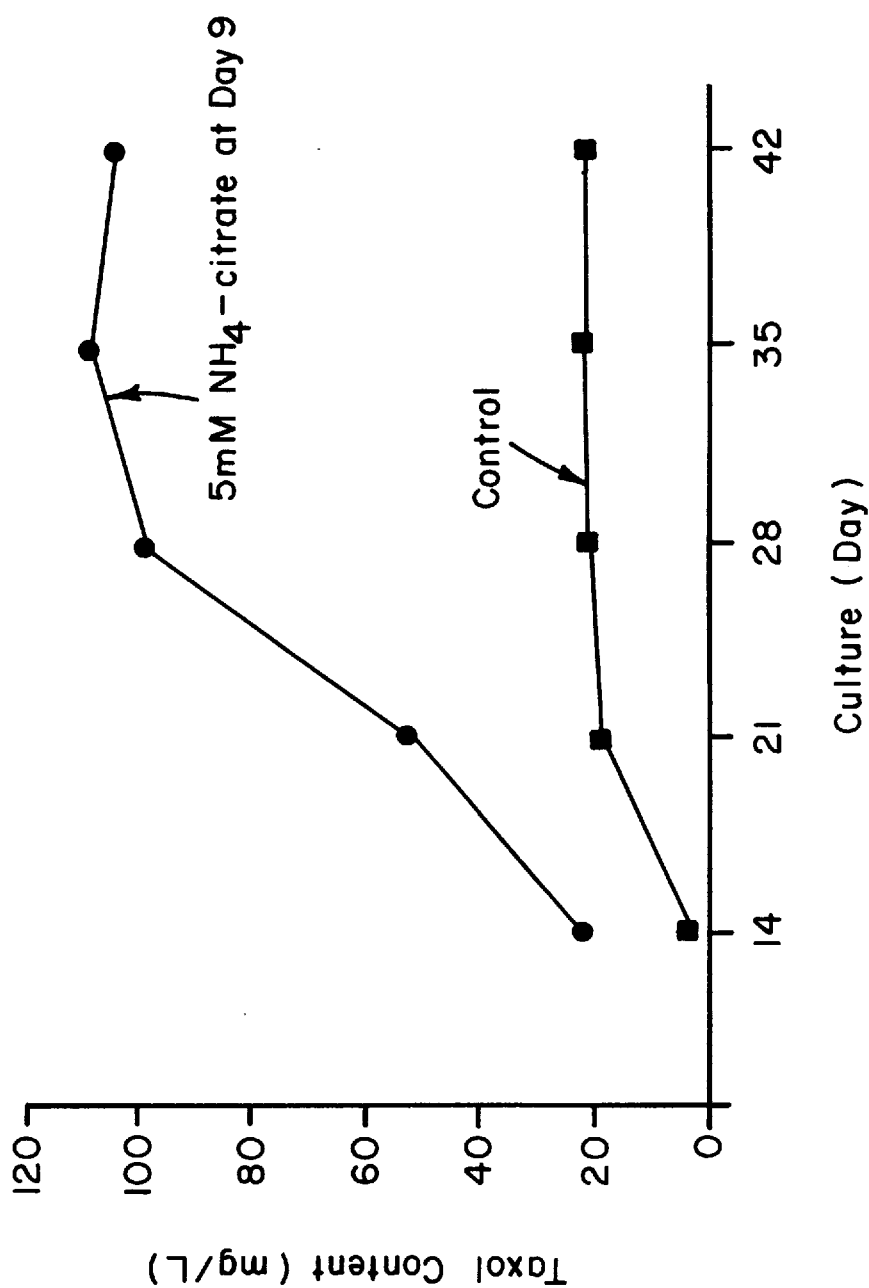
FIG. 2 is a graph showing the effect of $NH_4$-citrate on the taxol productivity.

The productivity of taxol in a suspension culture of SYG-1 was monitored, after the addition of NH$_4$-citrate. To a 250 ml of Erlenmeyer flask was poured 75 ml of B5 medium and 25 ml of 14 day old cell culture was inoculated into this medium, and incubated at the same growth condition described in Example 2. Then, 5 mM of NH$_4$-citrate was added to the culture after 9 days of incubation, and the taxol productivity was compared with a control in which NH$_4$-citrate was not added (see: FIG. 2). As can be seen in FIG. 2, it was determined that the amount of taxol produced was about 103.6 mg/L when NH$_4$-citrate was added to a medium (-●-), which was 4.9 times the control (-O-).

EXAMPLE 5

Effect of Maltose on the Taxol Productivity

It has been well known that the increase of sugar concentration in a plant cell culture leads to an increase in secondary metabolite production. For example, it has been reported that: addition of 3% (w/v) sucrose and 5% (w/v) mannitol has improved the productivity of antocyanin in callus culture of *Daucus carota* (see: Knobloch, K. -H., et al., Zeiteshrift fur Natruforschung, 35c:55–556 (1981)); and, 88 mM sucrose and 165 mM mannitol heightened the antocyanin productivity in a suspension culture of *Vitis vinifera* (see: Rajendran, L., et al., Biotechnology Letters, 14(8):707–712 (1992)). On the other hand, the decrease in the growth and the secondary metabolite production were also reported when the amount of sugar over a certain concentration was added, possibly due to osmotic stress (see: Do, C. B., and Cormier, F., Plant Cell Reports, 9:500–504 (1990)).

The effect of maltose addition to SYG-1 was evaluated.

Figure 3:
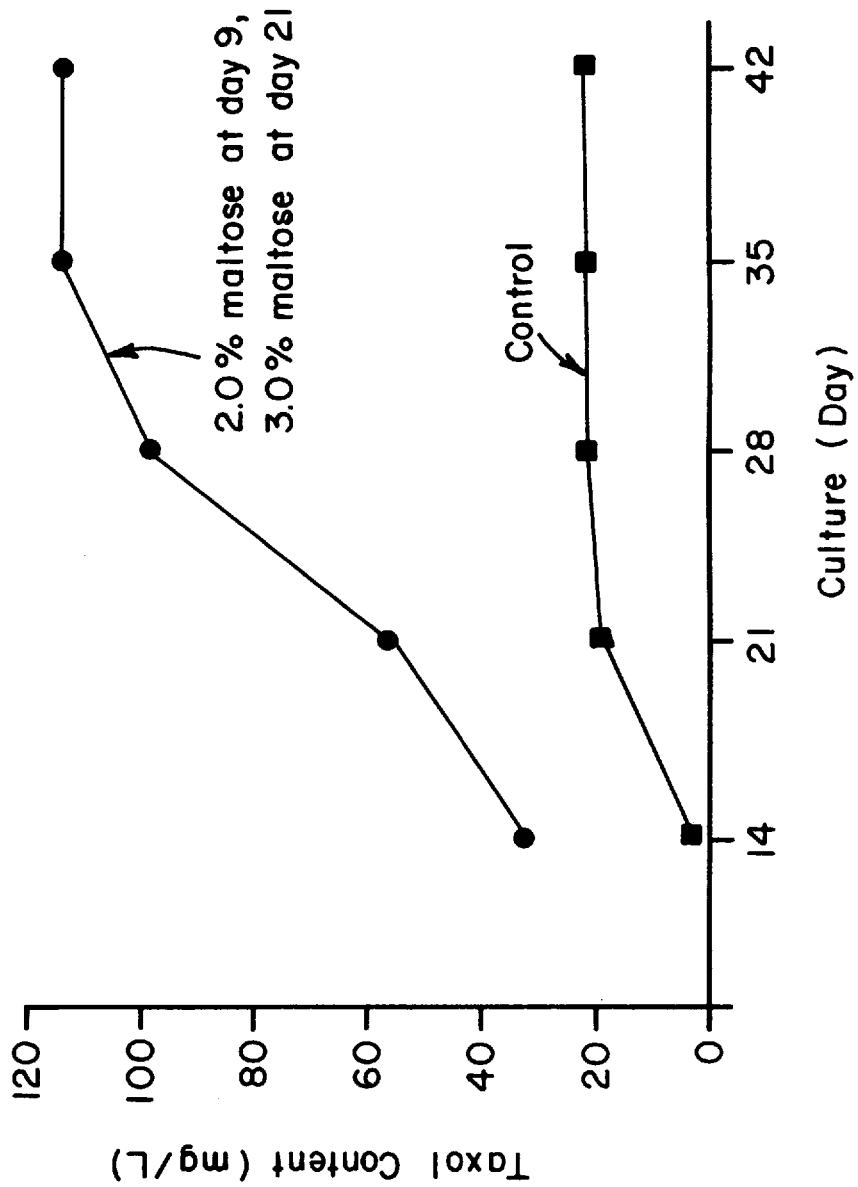
FIG. 3 is a graph showing the effect of maltose on the taxol productivity.

To a 250 ml of Erlenmeyer flask was poured 75 ml of B5 medium and 25 ml of 14 day old cell culture was inoculated into this medium, and incubated under the same growth condition described in Example 2. Then, 2% (w/v) and 3% (w/v) of maltose were added to the culture after 9 days and 21 days of incubation, respectively and the productivity of taxol was compared with a control which does not contain maltose (see: FIG. 3). As can be seen in FIG. 3, it was determined that the amount of taxol was 112.75 mg/L when maltose was added to a medium (-●-), which was 5.3 times the control (-O-).

EXAMPLE 6

Semi-continuous Culture of SYG-1

Based on the results obtained in Examples 2 to 5, taxol was prepared by employing semi-continuous culture of SYG-1.

Figure 4:
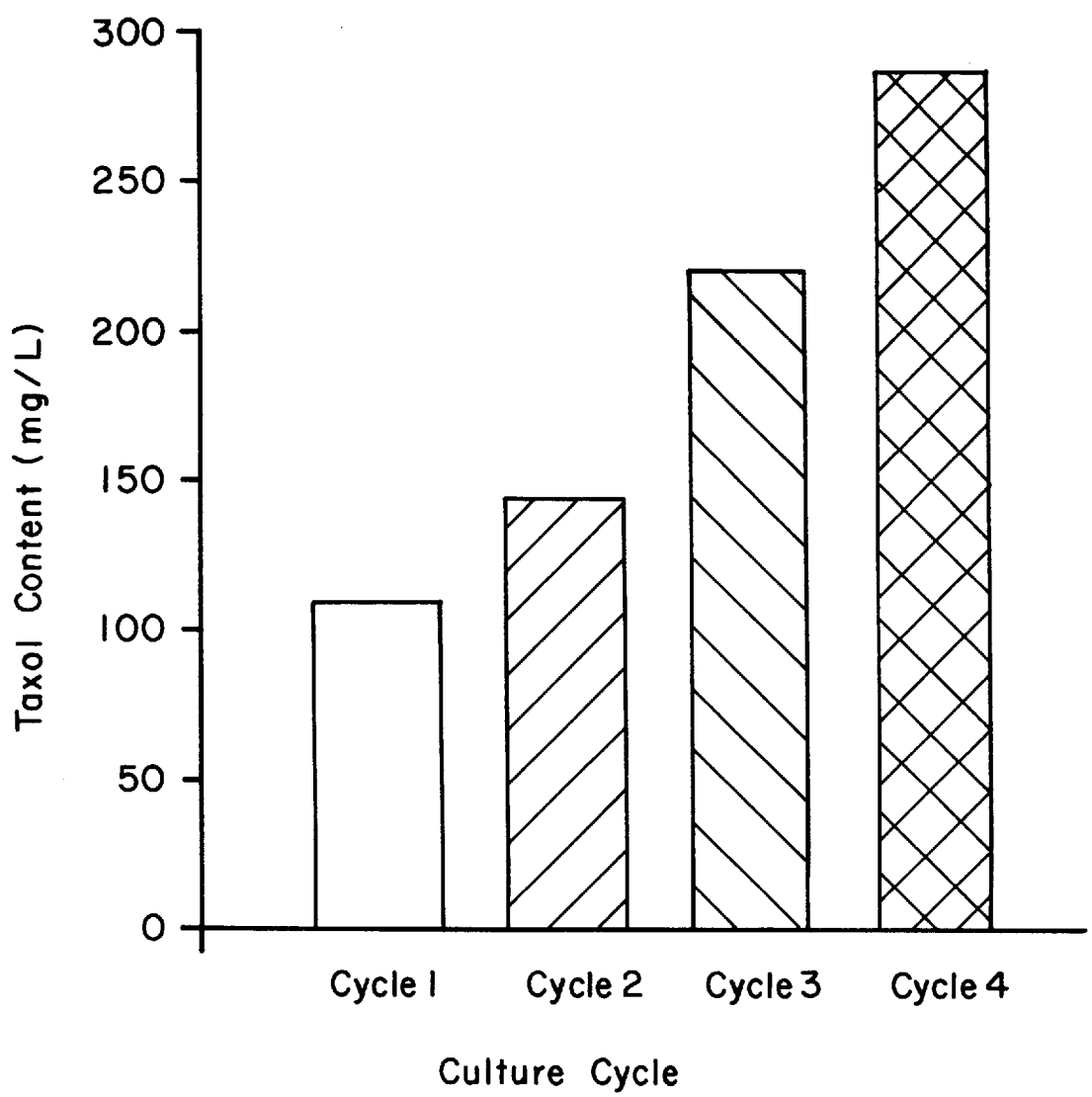
FIG. 4 is a graph showing the productivity of taxol in semi-continuous culture of SYG-1 in accordance with the culture cycle.

To a 250 ml of Erlenmeyer flask was added 80 ml of growth medium and 20 ml of 14 day old SYG-1 culture, 10 $\mu$M AgNO$_3$ was added at the beginning of culture, followed by the addition of 5 mM NH$_4$-citrate and 2% (w/v) maltose after 9 days of incubation. After 21 days of incubation, 20 ml of culture equivalent to 1/5 volume of total culture was transferred to other flask containing 80 ml fresh medium to start another cycle of culture. Then, to 80 ml of remnant culture equivalent to 4/5 volume of total culture, was added 3% (w/v) maltose, and incubated for additional 21 days in which taxol production is maximized. At this time, incubation was made at 24° C., and an agitation speed of 150 rpm. Culture samples were taken, periodically to check for microbial contamination. The amount of taxol produced in the culture was also determined by employing high performance liquid chromatography (HPLC, Waters, U.S.A.) described as above. As a result, microbial contamination was not observed and the productivity of taxol after 42 days incubation was determined to be 284 mg/L (see: FIG. 4). As can be seen in FIG. 4, taxol concentration was increased as the cycles of culture were repeated.

As clearly illustrated and demonstrated as aboves, the present invention provides a method for mass production of taxol by semi-continuous culture of Taxus genus plant with a high yield. According to the present invention, the productivity of taxol to the level of 300 mg/L, after 40 to 50 days incubation, was observed, when *Taxus chinensis* SYG-1 was employed in the semi-continuous culture with the addition of $AgNO_3$, $NH_4$-citrate and maltose to improve the productivity of taxol.

What is claimed is:

1. A method for mass production of taxol by semi-continuous culture of *Taxus chinensis* SYG-1 (KCTC 0232BP) which comprises the steps of:

(i) inoculating cells of *Taxus chinensis* SYG-1 (KCTC 0232BP) on a medium containing 1 to 10% (w/v) sugar, and incubating said cells;

(ii) transferring a part of the culture solution containing the *Taxus chinensis* SYG-1 (KCTC 0232BP) cells obtained in step (i) to a fresh medium for a volume ratio of said culture solution to said fresh medium to be in the range of 1/10 to 1/2 and repeating the incubation step (i);

(iii) adding sugar to the solution remaining after transfer of the solution from step (ii) at a concentration of 1 to 10% (w/v) and incubating said cells; and, (iv) recovering taxol from the culture solution in which said taxol is produced by said cells.

2. The method of claim 1, which further comprises a step of addition of $AgNO_3$, to the medium at a concentration of 1 to 15 $\mu$M at day 0 of the cell culture process.

3. The method of claim 1, which further comprises a step of addition of $NH_4$-citrate or maltose, or both, to the medium at a concentration of 1 to 15 mM and 1 to 10% (w/v), after 5 to 30 days of incubation, respectively.

4. The method of claim 1, wherein the incubation time of maximum production of taxol in step (iii) is 40 to 50 days from the beginning of the cell culture process.

* * * * *